(12) United States Patent
Mielcarz et al.

(10) Patent No.: US 11,129,950 B2
(45) Date of Patent: Sep. 28, 2021

(54) SYSTEM AND METHOD FOR MONITORING RESUSCITATION OR RESPIRATORY MECHANICS OF A PATIENT

(71) Applicants: THE GENERAL HOSPITAL CORPORATION, Boston, MA (US); Craig Mielcarz, Somerville, MA (US); Kevin Cedrone, Cambridge, MA (US); Data Santorino, Mbara (UG); Kristian Olson, Boston, MA (US)

(72) Inventors: Craig Mielcarz, Somerville, MA (US); Kevin Cedrone, Cambridge, MA (US); Data Santorino, Mbara (UG); Kristian Olson, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 870 days.

(21) Appl. No.: 14/443,405

(22) PCT Filed: Nov. 19, 2013

(86) PCT No.: PCT/US2013/070745
§ 371 (c)(1),
(2) Date: May 18, 2015

(87) PCT Pub. No.: WO2014/078840
PCT Pub. Date: May 22, 2014

(65) Prior Publication Data
US 2015/0283342 A1    Oct. 8, 2015

Related U.S. Application Data

(60) Provisional application No. 61/728,211, filed on Nov. 19, 2012.

(51) Int. Cl.
*A61M 16/00* (2006.01)
*G09B 23/28* (2006.01)
(Continued)

(52) U.S. Cl.
CPC ......... *A61M 16/0078* (2013.01); *A61B 5/087* (2013.01); *A61B 5/0935* (2013.01);
(Continued)

(58) Field of Classification Search
CPC ............ A61M 16/0078; A61M 16/021; A61M 16/0003; A61M 16/0051; A61M 2205/52;
(Continued)

(56) References Cited

U.S. PATENT DOCUMENTS

| 4,660,568 A | 4/1987 | Cosman |
| 4,797,104 A | 1/1989 | Laerdal et al. |

(Continued)

FOREIGN PATENT DOCUMENTS

| EP | 1767236 A2 | 3/2007 | |
| NL | WO 2010059049 A2 * | 5/2010 | ........... A61H 31/005 |

(Continued)

OTHER PUBLICATIONS

William C. Wilson, Christopher M. Grande, David B. Hoyt, "Trauma Critical Care", vol. 2, 2007.*

(Continued)

*Primary Examiner* — Tu A Vo
(74) *Attorney, Agent, or Firm* — Quarles & Brady LLP (57) ABSTRACT

A system and method for monitoring resuscitation and respiratory mechanics of a patient is provided. A pressure sensor detects air pressure within an air-flow path of a resuscitator and generates a first detection signal in response thereto. A flow-rate sensor detects the flow-rate within the air-flow path and generates a second detection signal In response thereto. A processor receives and processes the first and second detection signals using an algorithm to identify a ventilation rate, a lung pressure, and an air volume corresponding to the respiratory air. A report is generated of (Continued)

real-time feedback about respiration of the patient that includes the ventilation rate, lung pressure, and air volume.

14 Claims, 7 Drawing Sheets

(51) Int. Cl.
*A61B 5/087* (2006.01)
*A61B 5/093* (2006.01)
*A61B 5/085* (2006.01)
*A61M 16/04* (2006.01)

(52) U.S. Cl.
CPC .... *A61M 16/0003* (2014.02); *A61M 16/0051* (2013.01); *A61M 16/021* (2017.08); *G09B 23/288* (2013.01); *A61B 5/085* (2013.01); *A61M 16/04* (2013.01); *A61M 2016/0027* (2013.01); *A61M 2016/0033* (2013.01); *A61M 2016/0036* (2013.01); *A61M 2205/075* (2013.01); *A61M 2205/15* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/8206* (2013.01); *A61M 2205/8212* (2013.01)

(58) Field of Classification Search
CPC ............ A61M 16/04; A61M 2205/075; A61M 2016/0033; A61M 2205/15; A61B 5/0935; A61B 5/087; A61B 5/085; G09B 23/288
See application file for complete search history.

(56) References Cited

U.S. PATENT DOCUMENTS

| | | | |
|---|---|---|---|
| 6,758,216 B1 | 7/2004 | Berthon-Jones et al. | |
| 7,357,033 B2 | 4/2008 | Lau et al. | |
| 8,192,367 B2 | 6/2012 | Mykelbust et al. | |
| 2002/0026941 A1 | 3/2002 | Biondi et al. | |
| 2004/0249300 A1* | 12/2004 | Miller | A61B 5/085 600/532 |
| 2006/0011203 A1 | 1/2006 | Myklebust | |
| 2006/0111749 A1* | 5/2006 | Westenskow | A61M 16/00 607/5 |
| 2008/0053445 A1* | 3/2008 | Kroupa | A61M 16/0078 128/205.23 |
| 2008/0145827 A1 | 6/2008 | Strand et al. | |
| 2008/0214948 A1* | 9/2008 | Myklebust | A61B 5/087 600/538 |
| 2008/0302363 A1 | 12/2008 | Kroupa | |
| 2009/0071482 A1 | 3/2009 | Huddlestone | |
| 2010/0036266 A1* | 2/2010 | Myklebust | A61B 5/02444 600/500 |
| 2010/0256539 A1* | 10/2010 | Strand | A61H 31/005 601/41 |
| 2011/0282228 A1* | 11/2011 | Shiner | A61B 5/085 600/534 |
| 2011/0284004 A1* | 11/2011 | Silver | A61B 5/087 128/205.13 |
| 2012/0000470 A1 | 1/2012 | Milne et al. | |
| 2012/0097158 A1* | 4/2012 | Matalon | A61B 5/0002 128/202.18 |
| 2012/0097165 A1* | 4/2012 | Kuo | A61B 5/0836 128/205.13 |
| 2012/0272962 A1* | 11/2012 | Doyle | A61M 16/0051 128/204.23 |
| 2012/0302910 A1* | 11/2012 | Freeman | A61M 16/021 600/538 |
| 2012/0318266 A1* | 12/2012 | Chou | A61B 5/087 128/204.23 |
| 2013/0239960 A1* | 9/2013 | Bertinetti | A61M 16/0066 128/202.22 |
| 2014/0275820 A1* | 9/2014 | Varga | A61M 16/0078 600/301 |
| 2015/0096559 A1* | 4/2015 | Duval-Arnould | A61M 16/0084 128/202.22 |
| 2015/0144130 A1* | 5/2015 | O'Donnell | A61M 16/16 128/202.22 |

FOREIGN PATENT DOCUMENTS

| | | |
|---|---|---|
| NZ | 578601 A | 10/2011 |
| WO | 9841267 A1 | 9/1998 |
| WO | 0115761 A1 | 3/2001 |
| WO | 0143804 A1 | 6/2001 |
| WO | 0215968 A2 | 2/2002 |
| WO | 2006/088373 A1 | 8/2006 |
| WO | 2012/059049 A2 | 5/2010 |

OTHER PUBLICATIONS

International Search Report and Written Opinion dated Mar. 20, 2014 in connection with PCT/US2013/070745.
European Patent Office, Supplementary European Search Report, EP 13855912, dated Jun. 28, 2016.

* cited by examiner

SYSTEM AND METHOD FOR MONITORING RESUSCITATION OR RESPIRATORY MECHANICS OF A PATIENT

CROSS-REFERENCE TO RELATED APPLICATIONS

This application represents the national stage entry of PCT International Application No. PCT/US2013/070745 filed Nov. 19, 2013, which claims the benefit of U.S. Provisional Patent Application No. 61/728,211 filed on Nov. 19, 2012, the disclosures of which are incorporated by reference here in their entirety for all purposes.

STATEMENT REGARDING FEDERALLY SPONSORED RESEARCH

NA

BACKGROUND OF THE INVENTION

The present invention relates to systems and methods for monitoring resuscitation or respiratory mechanics of a patient or users. More particularly, the invention relates to systems and methods for identifying ventilation rate, lung pressure, and air volume of respiratory air. In addition a constitutive non-linear model of lung compliance may be employed.

A bag-valve-mask (BVM) resuscitator is a device used to deliver air to the lungs of an incapacitated patient, with the intention of providing life support. Conventional bag-valve-mask resuscitators include a compressible air bag that forces air out of an outlet port when squeezed, and accepts air in from an inlet port when released. Bag-valve-mask resuscitators may also include a one-way valve that permits air to pass from the bag towards the patient, and inhibits exhaled air from re-entering the bag. A conformable mask is pressed tightly against the patient's face around the mouth and nose to form an airtight seal and force the air into the respiratory tract. Several different sized masks are often used interchangeably, with the appropriate mask selected depending on the age and size of the patient. Alternatively, a BVM may be coupled to endotracheal or laryngeal tube rather than a face mask. Bag-valve-mask resuscitators are often equipped with an over-pressure safety regulator, and features for optionally connecting filters or oxygen supply lines.

While standard bag-valve-mask resuscitators can be used to provide effective life support, proper use is far from guaranteed. Data shows that even the most expertly-trained practitioners may fail to operate the device correctly approximately 20 percent of the time. A common mistake in bag-valve-mask resuscitator use is allowing air leaks by failing to seal the mask properly against the patient's face. Other common mistakes that result in ineffective resuscitation include blocked airways, incorrect ventilation frequency, and insufficient lung inflation.

Each of these common mistakes can result in death or brain damage to the patient. Recent data show that of the 6.9 million children under the age of 5 who die annually, more than 43 percent die in the first month of life. Breathing problems at the time of birth (i.e., asphyxia) account for a major portion of these deaths globally. Approximately 6 million babies born annually would avoid death or severe neurologic disability if provided effective breathing assistance i.e., ventilation) within one minute of birth.

Therefore, there is a need for systems and methods to improve the quality and effectiveness of resuscitation efforts in a time sensitive manner.

SUMMARY OF THE INVENTION

The present invention overcomes the aforementioned drawbacks by providing a system and method that incorporates a pressure sensor and flow-rate sensor into a resuscitator. In particular, the present invention can determine the ventilation rate, lung pressure, and air volume of respiratory air using an algorithm that relates the air pressure and air volume in terms of elasticity and provides real-time feedback about resuscitation quality and respiration of the patient in both clinical and training applications.

In accordance with one aspect of the invention, a device for monitoring respiration and resuscitation of a patient is disclosed. The device includes a housing having an inlet and an outlet configured to communicate respiratory air and connected by an air-flow path. The device also includes a pressure sensor configured to detect air pressure within the air-flow path and generate a first detection signal in response thereto. A flow-rate sensor is configured to detect flow-rate within the air-flow path and generate a second detection signal in response thereto. Further, a processor is configured to receive and process the first detection signal and the second detection signal using an algorithm to identify at least one of a ventilation rate, a lung pressure, or an air volume corresponding to the respiratory air. A feedback device is coupled to the processor and configured to generate a report of real-time feedback about respiration of the patient through the device including at least one of ventilation rate, lung pressure, or air volume.

In accordance with another aspect of the invention, a method for monitoring resuscitation performance of a patient coupled to a resuscitation device is disclosed. The method includes detecting an air pressure and a flow-rate of respiratory air moving through an air-flow path within a housing. The housing includes an inlet and an outlet having at least one of a pressure sensor or a flow-rate sensor positioned in the housing. A first detection signal is generated that indicates detected air pressure and a second detection signal is generated that indicates the flow-rate. The first detection signal and the second detection signal are processed using a non-linear model of lung compliance that relates the air pressure to the air volume in terms of elasticity to identify at least one of a ventilation rate, a lung pressure, or an air volume. A relative resuscitation performance is communicated in real-time based on the at least one of the ventilation rate, lung pressure, or air volume.

In accordance with another aspect of the invention, a retrofit device adapted for a resuscitator to monitor respiration of a patient is disclosed. The retrofit device includes a housing configured to be positioned between an inlet and an outlet of a resuscitator to have an air-flow path extend therethrough. The retrofit device also includes a pressure sensor supported by the housing and configured to detect air pressure within the air-flow path of the resuscitator and generate a first detection signal in response thereto. A flow-rate sensor is supported by the housing and configured to detect flow-rate within the air-flow path and generate a second detection signal in response thereto. In addition, a processor is configured to receive and process the first detection signal and the second detection signal using an algorithm to identify at least one of a ventilation rate, a lung pressure, or an air volume corresponding to respiratory air.

In accordance with another aspect of the invention, a training device for providing feedback about respiratory air of a patient during resuscitation is disclosed. The training device includes a pressure sensor configured to detect air pressure within an air-flow path of the training device and generate a first feedback signal in response thereto. A flow-rate sensor is configured to detect flow-rate within the air-flow path and generate a second feedback signal in response thereto. Further, a processor is configured to receive and process the first feedback signal and the second feedback signal using an algorithm to identify at least one of a ventilation rate, a lung pressure, or an air volume corresponding to the respiratory air. A user interface is coupled to the processor and configured to generate a report of real-time data or pre-acquired data about respiration of the patient through the training device including the at least one of the ventilation rate, lung pressure, or air volume. The real-time data or the pre-acquired data is then compared to resuscitation training information.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
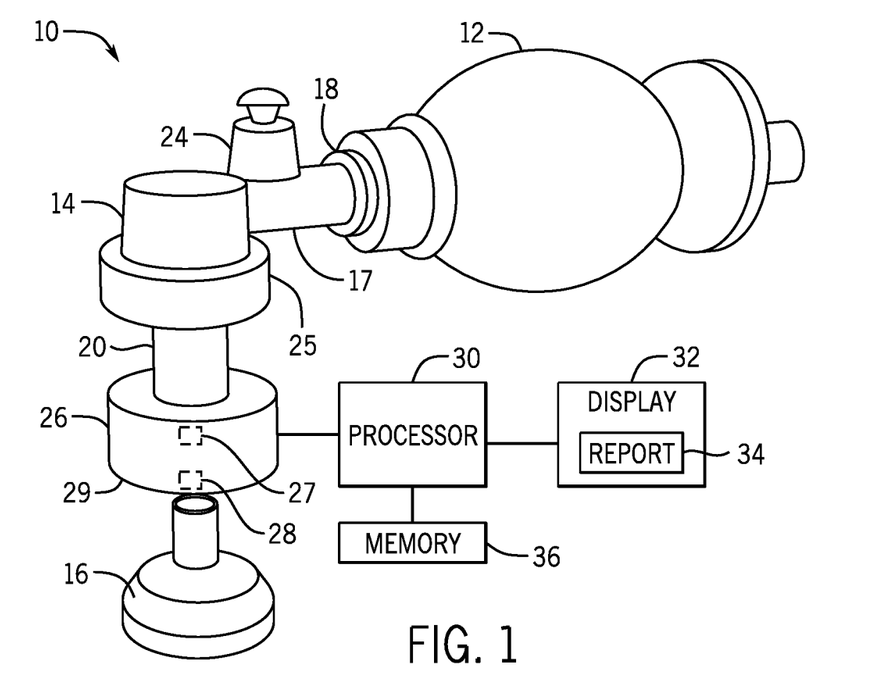
FIG. 1 is a perspective view of a resuscitation device including a pressure sensor and configured to implement the present invention.
Figure 2:
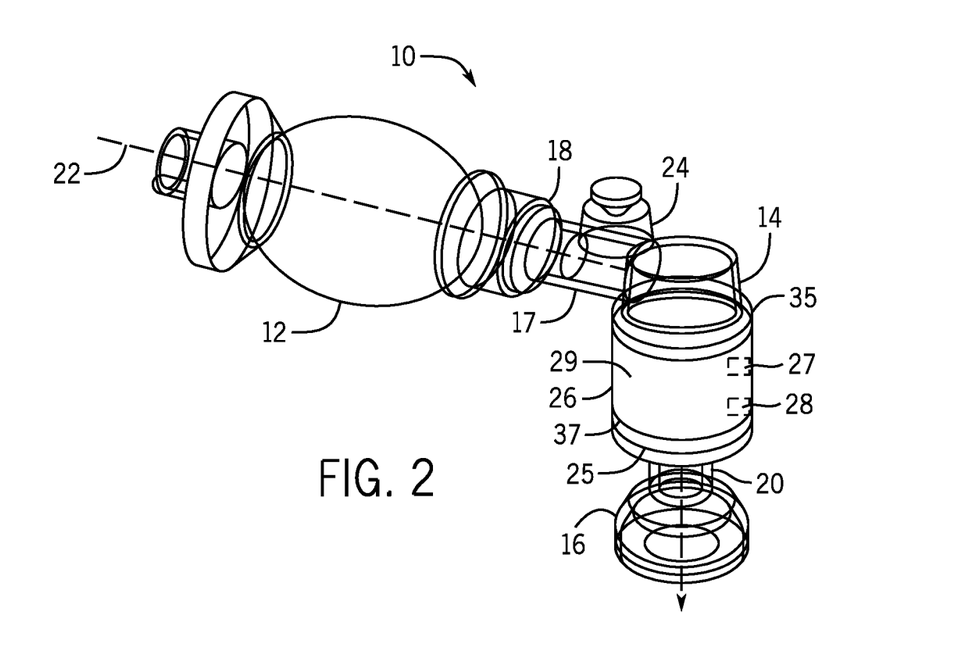
FIG. 2 is a perspective view of the resuscitation device of FIG. 1 showing an air flow path.

Referring particularly now to FIGS. 1 and 2, a resuscitation device 10 is shown that is configured to measure air pressure and flow-rate over time during a resuscitation process of a patient or a simulation for training purposes. The resuscitation device 10 may include or be adapted to include, for example, a standard bag-valve-mask (BVM) resuscitator, such as illustrated. The resuscitation device 10 may also be integrated with or utilize non-standard or proprietary resuscitator systems. For example, as will be described, the device 10 may be adapted or with components to function as a ventilator. In the resuscitation device 10 illustrated in FIGS. 1 and 2, the device includes an air bag 12 and a ventilation mask 16. The resuscitation device 10 may incorporate a standard BVM resuscitator, that includes the air bag 12 and ventilation mask 16. In some configurations, device may include an endotracheal tube or laryngeal mask airway. Without the present invention integrated therewith, the air bag 12 and ventilation mask 16 are coupled to opposite ends of a housing 14. The housing 14 is made up of a neck 17 providing an inlet 18 that is connected to the air bag 12, and an outlet 20 that is connected to the ventilation mask 16. An air-flow path 22, as shown in FIG. 2, connects the inlet 18 and the outlet 20 of the housing 14. A pressure release valve 24 may be coupled to or contained within the housing 14 to release excess system pressure often above 35-40 cm of water, for example, in the patient that could damage the lungs. A one-way valve 25 may be located in the housing 14 to permit air entry into patient's lungs and prevent exhaled air from returning to the housing 14 and the air bag 12. In accordance with the present invention, a sensor system 26 may be disposed in the air-flow path, such as between the outlet 20 and ventilation mask 16, as illustrated in FIG. 1. Alternatively, the sensor system 26 may be disposed in the air-flow path 22, such as between the housing 14 and the outlet 20, as illustrated in FIG. 2. While this configuration is advantageous for retrofitting the sensor system 26 to an existing resuscitator, such as illustrated, the sensor system 26 may be arranged anywhere within the air-flow path 22 and may be integrated with any of a variety of components of a resuscitation device 10.

The sensor system 26 may include a variety of components, as will be described. For example, the sensor system 26 may include a pressure sensor 27 to detect air pressure within the air-flow path 22. Also, the sensor system 26 may include a flow-rate sensor 28 disposed in the air-flow path 22 to detect flow-rate within the air-flow path 22. These and any other components, such as will be described, may be integrated within a housing 29 of the sensor system 26.

Figure 9:
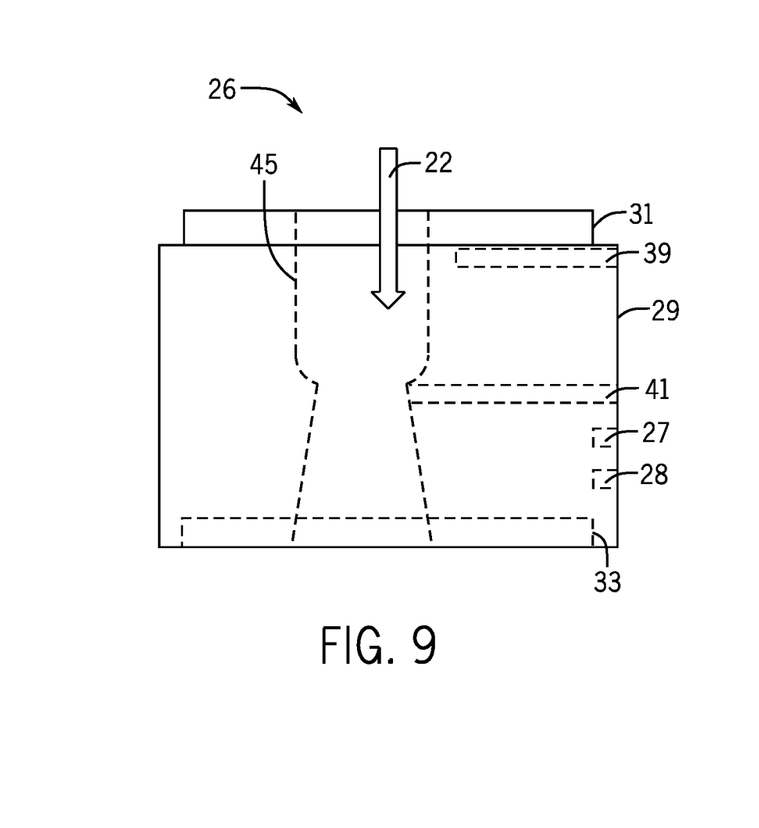
FIG. 9 is a cross-sectional view of a sensor system incorporated into the resuscitation device of FIG. 1.

Referring now to FIGS. 9-12, different configurations of the sensor system 26 are shown. As shown in FIG. 9, the housing 29 of the sensor system 26 includes the pressure sensor 27, the flow-rate sensor 28, and a port 45 extending through the housing 29 along the air flow path 22. The housing 29 may include male threads 31 on a top portion of the housing 29 and female threads 33 on a bottom portion of the housing 29. The male threads 31 and the female threads 33 are configured to engage female threads 35 and male threads 37, respectively, of the housing 14, as shown in FIG. 2. Other connection mechanisms are possible for coupling the sensor system 26 to the housing 14. The sensor system 26, as shown in FIG. 9, may include a first port 39 and a second port 41. The first port, for example, may be a high pressure sampling port configured to receive a venturi or Dall tube, for example. The second port 41, for example, may be a low pressure sampling port configured to receive a venturi or Dall tube, for example.

Figure 10:
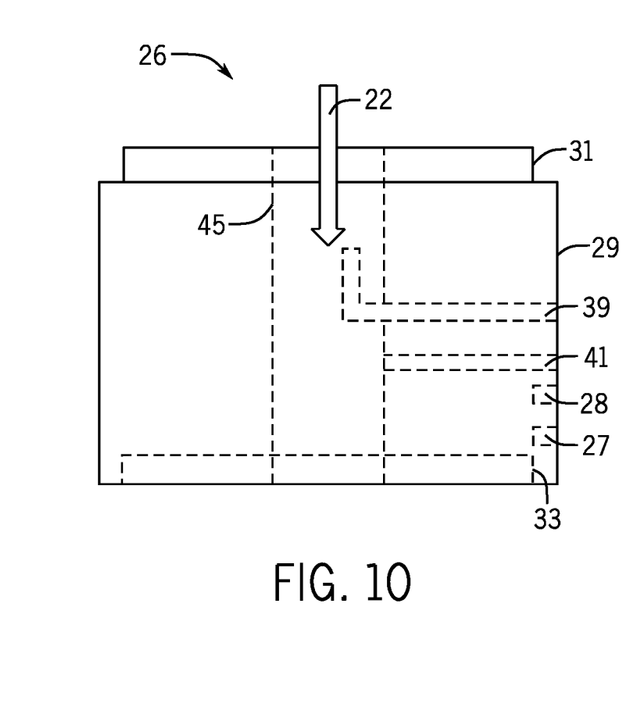
FIG. 10 is a cross-sectional view of a different sensor system incorporated into the resuscitation device of FIG. 1.

As shown in FIG. 10, the housing 29 of the sensor system 26 includes the pressure sensor 27, the flow-rate sensor 28, and a port 45 extending through the housing 29 along the air flow path 22. The housing 29 may include male threads 31 on the top portion of the housing 29 and female threads 33 on the bottom portion of the housing 29. The male threads 31 and the female threads 33 are configured to engage female threads 35 and male threads 37, respectively, of the housing 14, as shown in FIG. 2. Other connection mechanisms are possible for coupling the sensor system 26 to the housing 14. The sensor system 26, as shown in FIG. 10, may include a first port 39 and a second port 41. The first port, for example, may be a dynamic pressure sampling port configured to receive a pitot tube, for example. The second port 41, for example, may be a static pressure sampling port.

Figure 11:
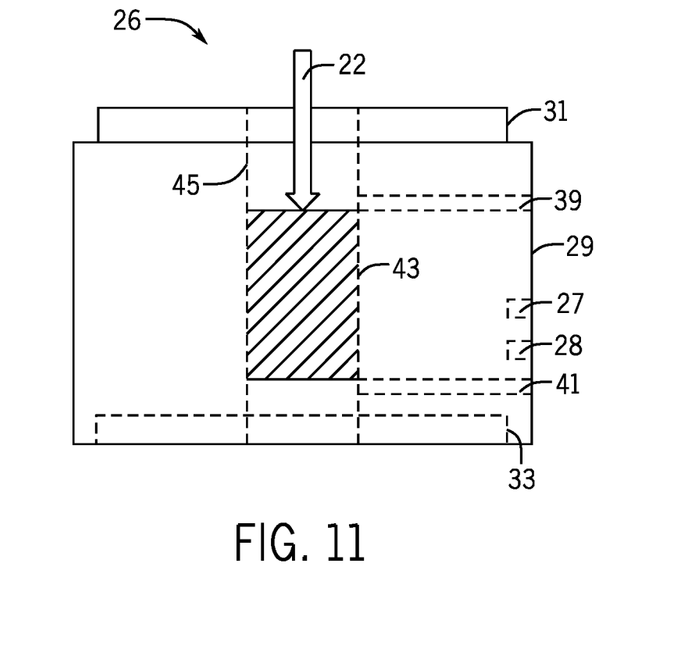
FIG. 11 is a cross-sectional view of yet a different sensor system incorporated into the resuscitation device of FIG. 1.

Referring now to FIG. 11, the housing 29 of the sensor system 26 includes the pressure sensor 27, the flow-rate sensor 28, and a port 45 extending through the housing 29 along the air flow path 22. The housing 29 may include male threads 31 on the top portion of the housing 29 and female threads 33 on the bottom portion of the housing 29. The male threads 31 and the female threads 33 are configured to engage female threads 35 and male threads 37, respectively, of the housing 14, as shown in FIG. 2. Other connection mechanisms are possible for coupling the sensor system 26 to the housing 14. The sensor system 26, as shown in FIG. 11, may include a first port 39 and a second port 41. The first port, for example, may be a high pressure sampling port, and the second port 41 may be a low pressure sampling port. A differential pressure element 43 may be positioned between the first port 39 and the second port 41 and configured to measure differential pressure. The differential pressure element 43 may be, for example, a laminar flow element or an orifice.

Figure 12:
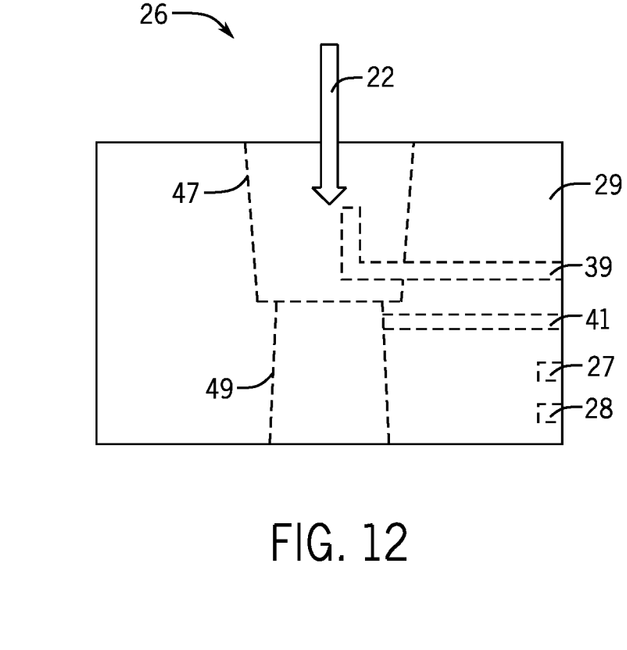
FIG. 12 is a cross-sectional view of a different sensor system incorporated into the resuscitation device of FIG. 1.

As shown in FIG. 12, the housing 29 of the sensor system 26 includes the pressure sensor 27 and the flow-rate sensor 28. The housing 29 may include a first tapered port 47 on the top portion of the housing 29 and a second tapered port 49 on the bottom portion of the housing 29. The first tapered port 47 and the second tapered port 49 extend through the housing 29 along the air flow path 22 are configured to engage the outlet 20 and the ventilation mask 16, respectively, as shown in FIG. 1. Other connection mechanisms are possible for coupling the sensor system 26 to the outlet 20 and the ventilation mask 16. The sensor system 26, as shown in FIG. 12, may also include a first port 39 and a second port 41. The first port, for example, may be a dynamic pressure sampling port configured to receive a pilot tube, for example. The second port 41, for example, may be a static pressure sampling port.

In operation, the air pressure and flow-rate detected by the pressure sensor 27 and the flow-rate sensor 28 may generate detection signals. For example, the signals may be generated on a continuous or discrete basis and communicated to a processor 30. The processor 30 may be configured to determine resuscitation quality in terms of a ventilation rate, a lung pressure, and an air volume using an algorithm. A display 32, for example, such as a liquid crystal display (LCD), light emitting diode (LED) display, an electronic paper display (e.g., E-Ink) or other display including colored lights, discrete sounds, or the like, may be coupled to the processor 30 to communicate a report 34 to the user. The report 34 may include real-time feedback about respiration of the patient, either inhaled or exhaled, through the resuscitation device 10. The report 34 and any of the detected signals may be stored to a memory 36 for later analysis and reporting, for example.

Figure 3:
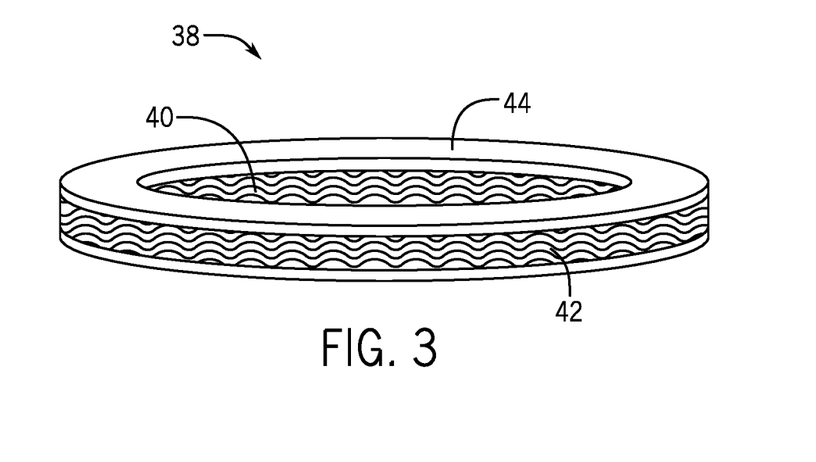
FIG. 3 is a perspective view of the pressure sensor of FIG. 1.
Figure 4:
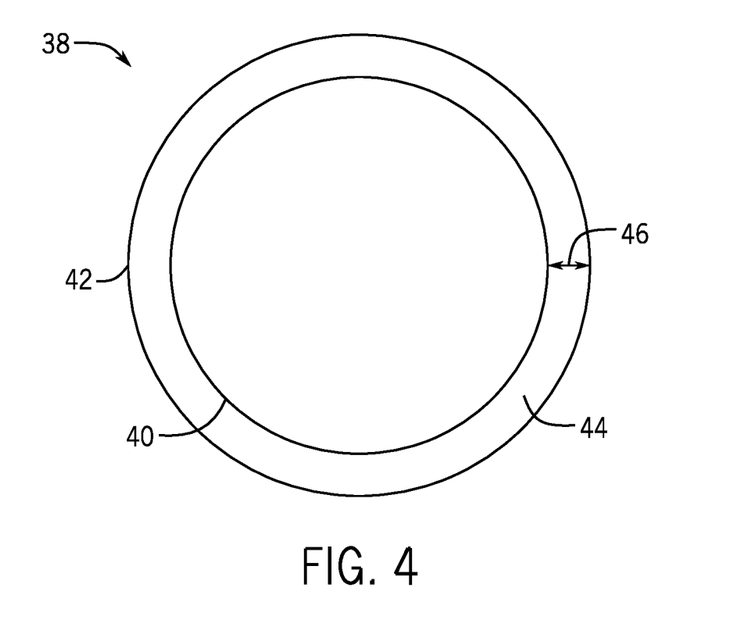
FIG. 4 is a top view of the pressure sensor of FIG. 3.

The pressure sensor 27 may be, for example, a capacitive pressure sensor, a hall effect sensor, a photo-diode emitter and receiver configuration, a differential pressure sensor, a strain-based sensor, a custom sensor, or a flexible diaphragm instrumented by capacitive or inductive means. The pressure sensor 27 may be configured to measure absolute pressure, gauge pressure of the respiratory air in the air-flow path 22 relative to atmospheric pressure, or differential pressure between both sides of the one-way valve 25 within the housing 14. In a non-limiting example, as shown in FIGS. 3 and 4, the pressure sensor is a capacitive pressure transducer 38. The capacitive pressure transducer 38 may include a first capacitive plate 40 having a metal-plated interior surface, as shown in FIG. 3, and a second capacitive plate 42 having a metal-plated exterior surface. An insulating material 44, for example a compliant dielectric material (e.g., silicone rubber, foam, sponge, gel, and the like), may be positioned between the first capacitive plate 40 and the second capacitive plate 42. As the air pressure within the air-flow path of the resuscitator housing varies, the thickness 46 and the capacitance of the capacitive pressure transducer 38 varies, as shown in FIG. 4. It is desirable, for example, for the capacitive pressure transducer 38 to have a high dielectric constant in order to maximize capacitance, and a low durometer measurement (i.e., material hardness) to maximize the change in thickness 46 due to the air pressure. Alternatively, in the case of the resuscitation device 10 being used as a training device, a commercially available Micro-electro-mechanical systems (MEMS) sensor, for example, may be used as the pressure sensor 27.

Returning now to FIG. 2, the flow-rate sensor 28 may be, for example, a hot wire or hot film anemometer, a rotating vane anemometer, a mechanical switch, an optical switch, cold-wire inductance oscillator, a laminar flow element differential pressure, vortex flow sensor, ultrasonic flow sensor, venturi differential pressure, pitot-static tube configuration, orifice plate differential pressure, Dall tube, spring-loaded vane- or flap-type air flow meter. The flow-rate sensor 28 may be configured to measure air-flow through the one-way valve 25, air-flow from the air bag 12 to the inlet 18 of the housing, or air-flow out of an overpressure regulator, for example.

Positioning of the pressure sensor 27 and the flow-rate sensor 28 within the housing 14 of the resuscitation device 10 may vary. As shown in FIG. 2, both the pressure sensor 27 and the flow-rate sensor 28 are positioned upstream of the one-way valve 25. Alternatively, both the pressure sensor 27 and the flow-rate sensor 28 may be positioned either proximal or distal, from the ventilation mask 16 of the one-way valve 25 located within the housing 14. In yet another alternative embodiment, the pressure sensor 27 and the flow-rate sensor 28 may be split between upstream and downstream of the one-way valve 25. The pressure sensor 27 and the flow-rate sensor 28 may also be integrated beside the pressure release valve 24, or, as mentioned above, may be part of a retrofit device.

Figure 6:
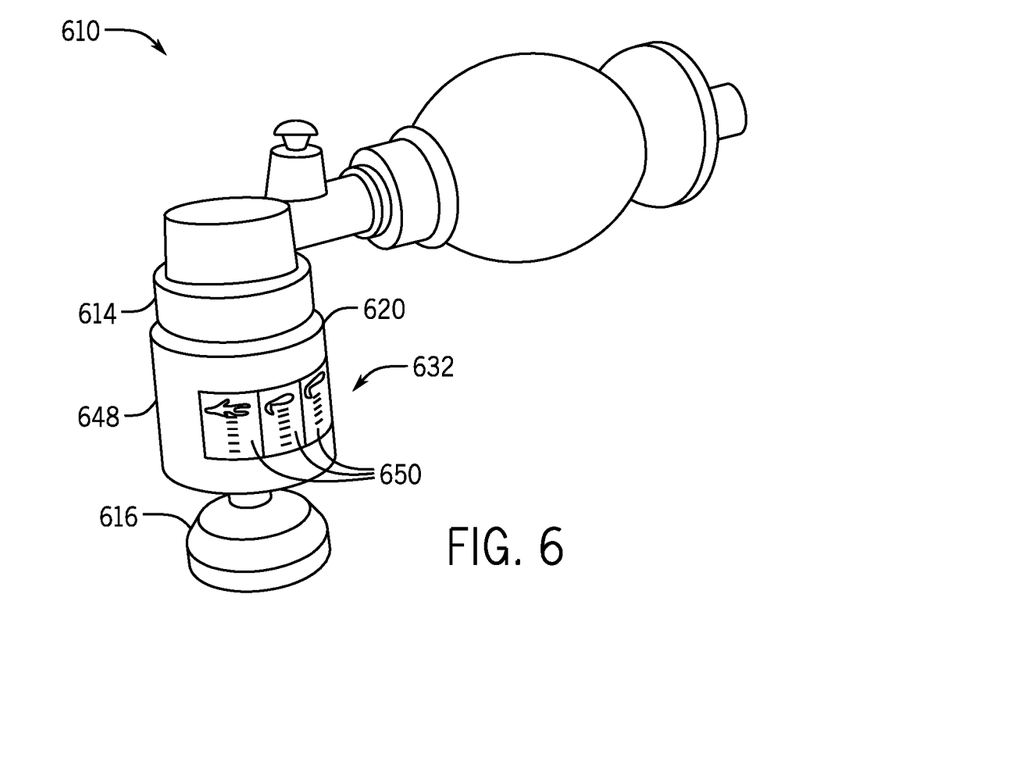
FIG. 6 is a perspective view of a resuscitation device having indicators on a user interface according to another embodiment of the present invention.

For example, FIG. 6 provides one illustration of a retrofit device 648 that also includes the processor 30 and display 32. The retrofit device 648 as shown in FIG. 6, may be an add-on device that may be coupled to existing resuscitation equipment 610, for example. The retrofit device 648 may be coupled between the outlet 620 of the housing 614 and the ventilation mask 616, for example. The display 632 may include a plurality of indicators 650 to indicate when the ventilation rate, the lung pressure, air volume, or combination thereof is either above or below a predetermined value, thereby indicating a blocked airway, an air leak in the air-flow path, or insufficient operator ventilation pressure, for example. If the ventilation rate is outside the range of 30-60 breaths per minute in newborn babies, for example, one of the plurality of indicators 650 will communicate an alert to the user. If the lung pressure, for example, is outside the range of 10-15 cm of water after initial lung inflation in a term baby one of the plurality of indicators 650 will communicate an alert to the user. In addition, if the air volume is outside the range of 4-6 milliliters per kilogram, for example, one of the plurality of indicators 650 will communicate an alert to the user.

The above-described alerts provide real-time feedback to the user and may be, for example, a visual alert, an audible alert, a vibratory alert, or a combination there of. The alerts may notify the user of improper use of the resuscitation device during an actual resuscitation, for example, thereby prompting the user to provide immediate corrective action. As shown in FIG. 6, the plurality of indicators 650 are lights that provide a visual alert. The lights may be different colors, for example, to represent different characteristics of the respiration of the patient. Other visual indicators may include, but are not limited to a mechanical dial or a rotating needle. Audible alerts may also be generated, for example, an audible buzzer or speaker that varies in pitch and beat rate to convey changes in the characteristics (i.e., the ventilation rate, lung pressure, air volume) of the respiration of the patient. For example, if the flow-rate is increasing, the audible alert may increase in pitch, beat rate, or combination thereof.

Figure 7:
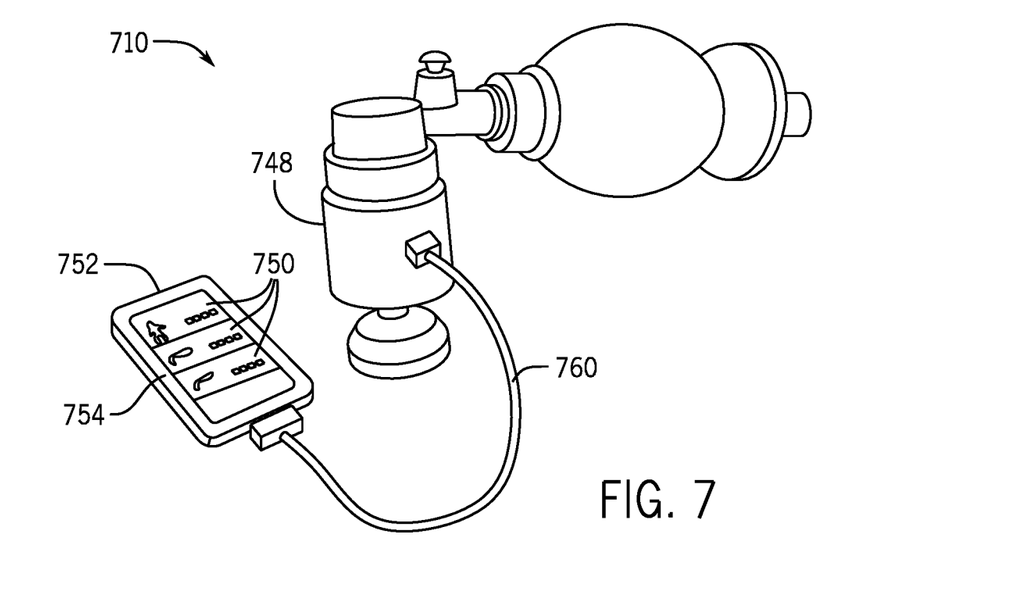
FIG. 7 is a perspective view of a resuscitation device coupled to a wireless device for displaying feedback related to the respiration of the patient according to another embodiment of the present invention.

Referring now to FIG. 7, a retrofit device 748 may, additionally or alternatively, provide the plurality of indicators 750 on a separate device 752, such as a mobile device, laptop, personal computer, or tablet, for example. The separate device 752 may have a wired connection 760 that connects the separate device 752 to retrofit device 748. Alternatively, the separate device 752 may be wirelessly connected to the retrofit device 748. The separate device 752 may include a user interface 754 allowing a user to access previously acquired data (i.e., ventilation rates, lung pressures, air volumes, etc.) of a resuscitation process from the memory 36, as shown in FIG. 1. The previously acquired data may be compared to resuscitation training material, for example, thereby using the resuscitation device as a training device for the user.

Figure 8:
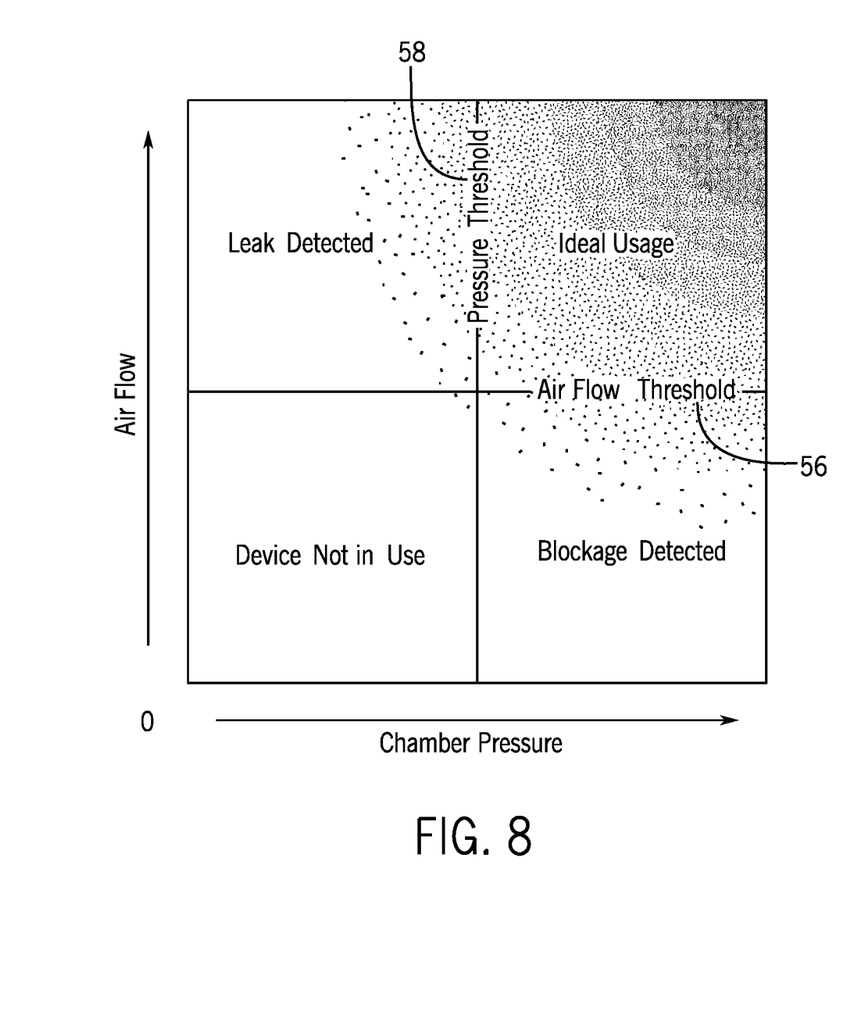
FIG. 8 is a graph showing the relationship between flow-rate and air pressure of respiratory air within the resuscitation device of FIG. 1.

The graph shown in FIG. 8 represents the thresholds for when the plurality of indicators 650 and 750 shown in FIGS. 6 and 7, are displayed to the user. For example, if the flow-rate detected by the flow-rate sensor is below an air-flow threshold 56 (e.g., 2 milliliters per kilogram) and the air pressure detected by the pressure sensor is below a pressure threshold 58 (e.g., 4 cm of water, none of the plurality of indicators will be activated, thereby indicating the resuscitation device is inactive, or the resuscitation device is in a low-power "sleep" mode to save battery life, for example. If, for example, the flow-rate detected by the flow-rate sensor is below the air-flow threshold 56 and the air pressure detected by the pressure sensor is above the pressure threshold 58, one of the plurality of indicators will be activated and indicate to the user that an airway blockage is detected. Alternatively, if the flow-rate detected by the flow-rate sensor is above the air-flow threshold 56 and the air pressure detected by the pressure sensor is below the pressure threshold 58, one of the plurality of indicators will be activated and indicate to the user that an air leak is detected in the air-flow path. If the flow-rate detected by the flow-rate sensor is above an air-flow threshold 56 (e.g., 4 milliliters per kilogram) and the air pressure detected by the pressure sensor is above the pressure threshold 58 (e.g., 8 milliliters per kilogram), the plurality of indicators will be activated to indicate the resuscitation device is being used properly and effective resuscitation is being provided to the patient. Both the air-flow threshold 56 and the pressure threshold 58 may be programmable and adjusted depending on the clinical application that the resuscitation device is being used for.

Thus, the resuscitation device may provide different feedback parameters to the user depending on different training or use scenarios, such as different life support techniques. For example, a resuscitation trainer may receive data related to the air pressure, flow-rate and wave forms from the resuscitation device in order to coach users in real-time, or data related to the air pressure, flow-rate, and wave forms may be stored to the memory and reviewed for more summary training improvements, for example. Alternatively, for a resuscitation trainee or real-time user of the resuscitation device, the data (i.e., ventilation rates, lung pressures, air volumes, etc.) may be displayed within or outside of acceptable ranges, as previously described. Alternatively, standardized queries with thresholds of acceptable parameters of ventilation rates, lung pressures, air volumes, etc., may be utilized for resuscitation examinations or certifications. These thresholds may be deemed to have been sufficiently met by either reaching each, reaching each simultaneously, or by meeting an absolute or percentage time within an acceptable range.

The above-described resuscitation devices 10, 610, and 710 may be used on models or manikins as a training device, for example, or on patients such as neonates, infants, pediatrics, adults, and animals. The real-time feedback from the resuscitation device may be advantageous for users such as emergency medical technicians (EMTs), paramedics, physicians assistants, nurse practitioners, doctors, nurses, midwives, and birth-attendants for diagnosis of chronic obstructive pulmonary disease (COPD), asthma, bronchitis, pneumonia, surfactant deficiency, airway compromise, and supra-pulmonary airway obstruction, for example. Other non-medical users, such as singers, athletic trainers, and athletes may benefit from the real-time feedback of the resuscitation device used not for resuscitation but rather to measure lung mechanics.

In the case of medical uses, for example, the resuscitation device may be larger for pediatrics and adults compared to the resuscitation device used for infants or neonates. The resuscitation device for pediatric and adults may include added features of more accurate volume calculation utilizing either hardware bags external to the patient, user, or inflatable objects. Displacement and stretch sensors may be attached to the device, such as to the air bag 12, as well as user "exit" sensors configured to calculate air pressure, flow-rate and air volume. In essence, the device may be viewed as turning the resuscitation device 10 of FIG. 1 around and sensing the time and rates of air pressure and air-flow coming from the patient, rather than from the bag-valve-mask resuscitator. Estimation of forced expiratory volume in one second (i.e., FEV1), functional vital capacity (FVC), peak flow, respiratory rate (RR), and volume inflated or exhaled, for example, may also be obtained. For individual users, baseline or initial measurements may be compared to subsequent measurements over time to provide information about changes in the measurements over time.

Figure 5:
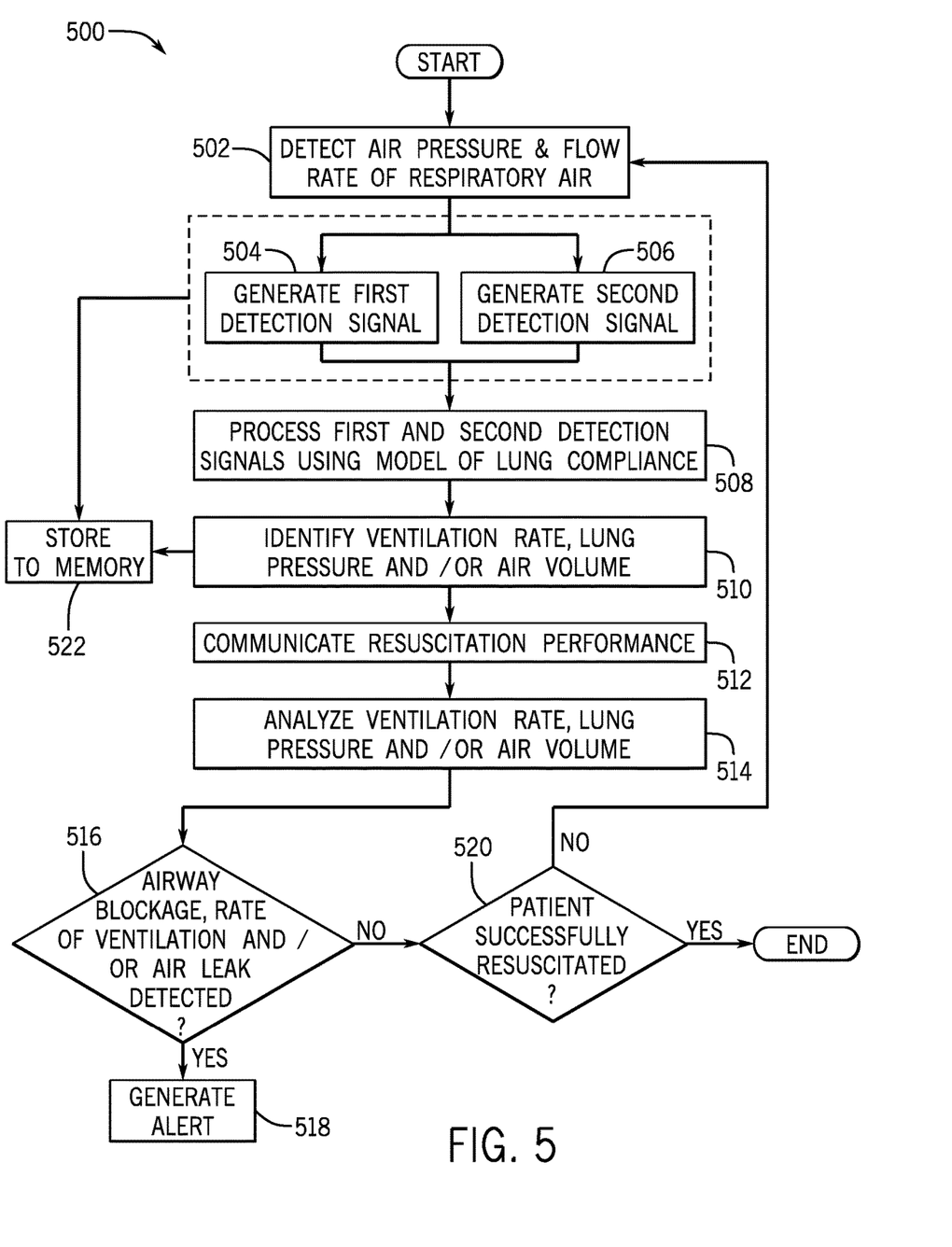
FIG. 5 is a flow chart setting forth the steps of the processes for providing real-time feedback about respiration of a patient in accordance with the present invention.

Referring now to FIG. 5, a flow chart setting forth exemplary steps 500 for monitoring resuscitation performance on a patient coupled to a resuscitation device in accordance with the present invention is provided. The following is an example and actual implementations may include all or some of these steps. For example, some implementations may only utilize some of the following processes to provide only some of the feedback or educational features described herein.

To start the process, the air pressure and flow-rate of respiratory air moving through the air-flow path within the housing is detected at process block 502. The air pressure and flow-rate are detected using the pressure sensor and flow-rate sensor positioned within the housing as described above. At process blocks 504 a first detection signal is generated indicating the detected air pressure from process block 502. Similarly, at process block 506 a second detection signal is generated indicating the detected flow-rate from process block 502. The processor 30, as shown in FIG. 1, then processes the first and second detection signals using a set of algorithms at process block 508. The algorithms, for example, are shown in the following mathematical formulas [1], [2], and [3] below:

$$C_L = \frac{\Delta V_L}{\Delta(P_{alv} - P_{pl})} \quad [1]$$

Where $C_L$ is lung tissue compliance, $V_L$ is lung volume, $P_{pl}$ is pressure in pleural space, and $P_{alv}$ is pressure in the alveoli.

$$G_L = \frac{\Delta V_L}{\Delta(P_{ao} - P_{alv})} \quad [2]$$

Where $G_L$ is airway conductance, $V_L$ is lung volume, $P_{ao}$ is pressure in the airway outlet, and $P_{alv}$ is pressure in the alveoli.

$$P_L = E_L(V_L - V_0) + R*V$$

Where $P_L$ is the transpulmonary pressure which is the sum of airway resistive pressure and pulmonary elastic pressure. $E_L$ is the lung elastance (i.e., $1/C_L$), and $R_L$ is the pulmonary resistance (i.e., $1/G_L$).

The algorithms used to process the first detection signal and the second detection at process block 508 may be, for example, a non-linear model of lung compliance that relates the air pressure and the air volume in terms of elasticity. Using the above described algorithms, the ventilation rate, lung pressure, and air pressure of the respiratory air of the patient may be identified at process block 510. The values of the ventilation rate, lung pressure, and air pressure may then be communicated in terms of relative resuscitation performance in real-time to the user at process block 512 and shown, for example, on the display 32 to the user, as shown in FIG. 1. At process block 514, the ventilation rate, lung pressure, and air pressure may be analyzed by the processor, for example, if an actual resuscitation process is being performed on the patient. However, if the resuscitation device is being used for training purposes, the trainee may be required to analyze the ventilation rate, lung pressure, and air pressure provided on the display.

Whether the trainee, for example, or the processor analyzes the displayed values of ventilation rate, lung pressure, and air pressure at process block 514, the values can be used to determine a potential blocked airway of the patient, a wrong rate of ventilation or an air leak caused by a break in the seal between the patient and the ventilation mask, for example, at process block 516. If a blocked airway, wrong ventilation rate, an air leak, or combination thereof is detected at process block 516, an alert is communicated to the user at process block 518. As previously described, the alert may be a visual alert, a vibratory alert, or an audible alert to communicate to the user that corrective action may be necessary to provide effective resuscitation. If no airway blockage or air leak is detected at process block 516, the user may determine if the patient has been successfully resuscitated at process block 520. If the patient has not been successfully resuscitated, the resuscitation device continues to detect the air pressure and flow-rate of respiratory air at process block 502 to ensure effective resuscitation is being performed, and the same process continues until the patient is successfully resuscitated. If the patient is successfully resuscitated at process block 520, then the process may end.

Optionally, at process block 522 the first and second detection signal generated at process blocks 504 and 506, respectively, may be stored to the memory 36, as shown in FIG. 1. Similarly, the ventilation rate, lung pressure, and air volume identified at process block 510 may be stored to memory at process block 522. Storing these parameters to memory allows users to access the data at a later time for training purposes or for analyzing a previous resuscitation event. If the stored data is used for training purposes, for example, the values for ventilation rate, lung pressure, and air volume may be compared to resuscitation training information to help the trainee and/or trainers better understand the resuscitation event.

Using the resuscitation device previously described may improve the speed and effectiveness of health worker training or re-training. With real-time guidance on their performance, trainees can more quickly hone their resuscitation skills. The resuscitation device provides real-time feedback during actual resuscitation when conditions could be different and more stressful than training. In addition, real-time feedback on the quality of ventilation facilitates immediate corrective action, possibly resulting in a greater number of lives saved or morbidity avoided. Further, audit data on ventilation proficiency allows trainers to identify persistent gaps in a trainee's resuscitation techniques, and more effectively target retraining and quality improvement measures.

The present invention has been described in terms of one or more preferred embodiments, and it should be appreciated that many equivalents, alternatives, variations, and modifications, aside from those expressly stated, are possible and within the scope of the invention.

The invention claimed is:

1. A device for monitoring respiration and resuscitation of a model or a patient, the device comprising:
   a housing having an inlet and an outlet configured to communicate respiratory air and connected by an air-flow path;
   a pressure sensor configured to detect air pressure within the air-flow path and generate a first detection signal in response thereto;
   a flow-rate sensor configured to detect flow-rate within the air-flow path and generate a second detection signal in response thereto;
   a processor configured to receive and process the first detection signal and the second detection signal over time using a non-linear model of lung compliance that relates the air pressure to an air volume to identify at least one of a lung pressure and the air volume corresponding to the respiratory air,
   the processor further configured to, based on values of the first detection signal and the second detection signal generated only during one of an inhale or an exhale:
   process the first detection signal with respect to a first threshold value, and process the second detection signal with respect to a second threshold value; and a feedback device comprising a plurality of indicators, the feedback device being coupled to the processor and configured to generate a report of real-time feedback about respiration of the model or patient including at least one of a ventilation rate, the lung pressure, the air volume, the blocked airway, and the air leak, the plurality of indicators being configured to indicate that there is an air leak in the air-flow path when the first detection signal is below the first threshold and the second detection signal is above the second threshold, the plurality of indicators being configured to indicate that an airway of the model or patient is blocked when the first detection signal is above the first threshold and the second detection signal is below the second threshold, the plurality of indicators being configured to indicate that the device is inactive or in a low-power sleep mode when the first detection signal is below the first threshold and the second detection signal is below the second threshold, and the plurality of indicators being configured to indicate that the device is being used properly and effective resuscitation is being provided when the first detection signal is above the first threshold and the second detection signal is above the second threshold.

2. The device as recited in claim 1, wherein the plurality of indicators is further configured to indicate when at least one of the ventilation rate, the lung pressure, and the air volume corresponding to the model or patient is above or below a predetermined value, the plurality of indicators being at least one of a visual indicator and an audible indicator.

3. The device as recited in claim 2, wherein the audible indicator is configured to vary in at least one of pitch, tone, and beat rate in response to changes in the at least one of the ventilation rate, the lung pressure, and the air volume.

4. The device as recited in claim 1, further comprising a ventilation mask configured to be received by at least one of a neonate, an infant, a pediatric patient, an adult patient, and an animal.

5. The device as recited in claim 1, further comprising a memory configured to store at least one of the first signal, the second signal, and the at least one of the ventilation rate, lung pressure, and air volume.

6. The device as recited in claim 5, further comprising a user interface configured to allow a user to access at least one of the ventilation rate, lung pressure, and air volume from the memory accompanied by resuscitation training information.

7. The device as recited in claim 1, wherein the respiration of the model or patient is monitored during a resuscitation process.

8. A method for monitoring resuscitation performance of a model or a patient coupled to a resuscitation device, the method comprising the steps of:

detecting an air pressure and a flow-rate of respiratory air moving through an air-flow path within a housing having an inlet and an outlet using at least one of a pressure sensor and a flow-rate sensor positioned in the housing;

generating a first detection signal indicating detected air pressure and a second detection signal indicating the flow-rate;

processing the first detection signal and the second detection signal over time using a non-linear model of lung compliance that relates the air pressure to an air volume to identify at least one of a lung pressure and the air volume based on values of the first detection signal and the second detection signal generated only during one of an inhale or an exhale, processing the first detection signal with respect to a first threshold value;

processing the second detection signal with respect to a second threshold value; and communicating, using a feedback device comprising a plurality of indicators, a relative resuscitation performance in real-time based on at least one of a ventilation rate, the lung pressure, and the air volume, the plurality of indicators indicating that there is an air leak in the air-flow path when the first detection signal is below the first threshold and the second detection signal is above the second threshold, the plurality of indicators indicating that an airway of the model or patient is blocked when the first detection signal is above the first threshold and the second detection signal is below the second threshold, the plurality of indicators indicating that the device is inactive or in a low-power sleep mode when the first detection signal is below the first threshold and the second detection signal is below the second threshold, and the plurality of indicators indicating that the device is being used properly and effective resuscitation is being provided when the first detection signal is above the first threshold and the second detection signal is above the second threshold.

9. The method as recited in claim 8, wherein communicating using the feedback device includes at least one of a visual communication and an audible communication.

10. The method as recited in claim 8, further comprising storing at least one of the first detection signal, the second detection signal, and the at least one of the ventilation rate, lung pressure, and air volume to a memory.

11. The method as recited in claim 10, further comprising accessing the at least one of the ventilation rate, lung pressure, and air volume from the memory and comparing the at least one of the ventilation rate, lung pressure, and air volume to a resuscitation training information.

12. A retrofit device adapted for a resuscitator to monitor respiration of a model or a patient, the retrofit device comprising:

a housing configured to be positioned between an inlet and an outlet of a resuscitator to have an air-flow path extend therethrough;

a pressure sensor supported by the housing and configured to detect air pressure within the air-flow path of the resuscitator and generate a first detection signal in response thereto;

a flow-rate sensor supported by the housing and configured to detect flow-rate within the air-flow path and generate a second detection signal in response thereto;

a processor configured to receive and process the first detection signal and the second detection signal using a non-linear model of lung compliance that relates the air pressure to an air volume to identify at least one of a lung pressure and the air volume corresponding to the respiratory air, the processor further configured to, based on values of the first detection signal and the second detection signal generated only during one of an inhale or an exhale:

process the first detection signal with respect to a first threshold value, and process the second detection signal with respect to a second threshold value; and a feedback device comprising a plurality of indicators, the feedback device being coupled to the processor, the plurality of indicators being configured to indicate that there is an air leak in the air-flow path when the first detection signal is below the first threshold and the second detection signal is above the second threshold, the plurality of indicators being configured to indicate that an airway of the model or patient is blocked when the first detection signal is above the first threshold and the second detection signal is below the second threshold, the plurality of indicators being configured to indicate that the device is inactive or in a low-power sleep mode when the first detection signal is below the first threshold and the second detection signal is below the second threshold, and the plurality of indicators being configured to indicate that the device is being used properly and effective resuscitation is being provided when the first detection signal is above the first threshold and the second detection signal is above the second threshold.

13. A training device for providing feedback about respiratory air of a model or a patient during resuscitation, the training device comprising:

a pressure sensor configured to detect air pressure within an air-flow path of the training device and generate a first feedback signal in response thereto;

a flow-rate sensor configured to detect flow-rate within the air-flow path and generate a second feedback signal in response thereto;

a processor configured to receive and process the first feedback signal and the second feedback signal using a non-linear model of lung compliance that relates the air pressure to an air volume to identify at least one of a lung pressure and the air volume corresponding to the respiratory air, the processor further configured to, based on values of the first detection signal and the second detection signal generated only during one of an inhale or an exhale:

process the first detection signal with respect to a first threshold value, and process the second detection signal with respect to a second threshold value; and a user interface comprising a plurality of indicators, the user interface being coupled to the processor and configured to generate a report of at least one of real-time data and pre-acquired data about respiration of the model or patient through the training device including at least one of a ventilation rate, the lung pressure, and the air volume, wherein the at least one of real-time data and pre-acquired data is compared to a resuscitation training information, the plurality of indicators being configured to indicate that there is an air leak in the air-flow path when the first detection signal is below the first threshold and the second detection signal is above the second threshold, the plurality of indicators being configured to indicate that an airway of the model or patient is blocked when the first detection signal is above the first threshold and the second detection signal is below the second threshold, the plurality of indicators being configured to indicate that the device is inactive or in a low-power sleep mode when the first detection signal is below the first threshold and the second detection signal is below the second threshold, and the plurality of indicators being configured to indicate that the device is being used properly and effective resuscitation is being provided when the first detection signal is above the first threshold and the second detection signal is above the second threshold.

14. The training device as recited in claim 13, wherein the user interface is communicatively coupled to a mobile device.

* * * * *

UNITED STATES PATENT AND TRADEMARK OFFICE
CERTIFICATE OF CORRECTION

PATENT NO. : 11,129,950 B2
APPLICATION NO. : 14/443405
DATED : September 28, 2021
INVENTOR(S) : Craig Mielcarz et al.

It is certified that error appears in the above-identified patent and that said Letters Patent is hereby corrected as shown below:

In the Specification

Column 4, Line 18, "hag" should be --bag--.

Signed and Sealed this
Twenty-first Day of February, 2023

*Katherine Kelly Vidal*

Katherine Kelly Vidal
*Director of the United States Patent and Trademark Office*